(12) United States Patent
Thor (10) Patent No.: US 12,396,635 B2
(45) Date of Patent: Aug. 26, 2025

(54) SYSTEM AND METHOD FOR VISUAL FIELD ASSESSMENT

(71) Applicant: Gautam Thor, La Jolla, CA (US)

(72) Inventor: Gautam Thor, La Jolla, CA (US)

(*) Notice: Subject to any disclaimer, the term of this patent is extended or adjusted under 35 U.S.C. 154(b) by 676 days.

(21) Appl. No.: 17/699,876

(22) Filed: Mar. 21, 2022

(65) Prior Publication Data

US 2022/0296092 A1 Sep. 22, 2022

Related U.S. Application Data

(60) Provisional application No. 63/163,511, filed on Mar. 19, 2021.

(51) Int. Cl.
| | |
|---|---|
| *A61B 3/024* | (2006.01) |
| *A61B 3/00* | (2006.01) |
| *A61B 3/032* | (2006.01) |
| *A61B 3/113* | (2006.01) |

(52) U.S. Cl.
CPC ............ *A61B 3/024* (2013.01); *A61B 3/0041* (2013.01); *A61B 3/032* (2013.01); *A61B 3/113* (2013.01)

(58) Field of Classification Search
CPC ....... A61B 3/024; A61B 3/0041; A61B 3/032; A61B 3/113; A61B 5/163; A61B 3/18
USPC ........................................................ 351/224
See application file for complete search history.

(56) References Cited

U.S. PATENT DOCUMENTS

| 10,275,024 B1* | 4/2019 | Simmons ................. G06F 3/013 |
| 2018/0008141 A1* | 1/2018 | Krueger ............... A61B 5/7257 |

OTHER PUBLICATIONS

Jian-Gang et al. Eye Gaze Estimation from a Single Image of One Eye; Proceedings of the Ninth IEEE International Conference on Computer Vision (ICCV 2003) 2-Volume Set 0-7695-1950-4/03 (Year: 2003).*
Jones et al. ; Portable Perimetry Using Eye-Tracking on a Tablet Computer—A Feasibility Assessment; Division of Optometry and Visual Science, School of Health Sciences, City, University of London, London, UK; Vision Science & Technology • Feb. 2019; (Year: 2019).*

* cited by examiner

*Primary Examiner* — Bumsuk Won
*Assistant Examiner* — Rahman Abdur
(74) *Attorney, Agent, or Firm* — Barry Choobin; Patent 360

(57) ABSTRACT

A system and method for assessing visual field of a subject eye for any blind spots. The method includes the steps of presenting a screen that is rendered as a grid, wherein points of the grids are spaced in units of visual angle. A visual focus point is presented on the screen on the screen and a visual stimulus moves on the screen consecutively while the subject eye focuses on the visual focus point and tracks the movement of the visual stimulus. When the visual stimulus enters a blind spot area in the visual field, the movement of the visual stimulus is perceived to be halted but is moving. Upon exiting the blind spot area, the halted visual stimulus is perceived to start moving again. Inputs from the user are taken when the above two events occur. Based on the inputs, the area of the blind spot is mapped.

20 Claims, 4 Drawing Sheets

Calculations for 27-inch monitor viewed from 36 inches (914 mm)

| Width of Full HD Screen pixels | Width of Screen in mm | Height & Width of each pixel mm | Height of Screen pixels | Height of Screen mm | Optimal Distance of Eye from Screen mm | Width of Moving-Box Row mm | Visual Angle degrees | Tangent of Visual Angle | Number of Boxes displayed progressively | Width of Box in mm | Width of Box in pixels |
|---|---|---|---|---|---|---|---|---|---|---|---|
| 1920 | 597 | 0.311 | 1080 | 336.0 | 914.4 | 194.4 | 12 | 0.2126 | 12 | 16.2 | 52 |
|  |  |  |  |  | 914.4 | 211.1 | 13 | 0.2309 | 13 | 16.2 | 52 |
|  |  |  |  |  | 914.4 | 228.0 | 14 | 0.2493 | 14 | 16.3 | 52 |
|  |  |  |  |  | 914.4 | 245.0 | 15 | 0.2679 | 15 | 16.3 | 53 |
|  |  |  |  |  | 914.4 | 262.2 | 16 | 0.2867 | 16 | 16.4 | 53 |
|  |  |  |  |  | 914.4 | 279.5 | 17 | 0.3057 | 17 | 16.4 | 53 |
|  |  |  |  |  | 914.4 | 297.1 | 18 | 0.3249 | 18 | 16.5 | 53 |
|  |  |  |  |  | 914.4 | 314.8 | 19 | 0.3443 | 19 | 16.6 | 53 |
|  |  |  |  |  | 36 inches |  |  | 102.7 mm |  |  |  |
|  |  |  |  |  |  |  |  | 6 degrees |  |  |  |

Fig. 4

SYSTEM AND METHOD FOR VISUAL FIELD ASSESSMENT

CROSS-REFERENCE TO RELATED APPLICATION

This application claims priority from the U.S. provisional patent application Ser. No. 63/163,511 filed on Mar. 19, 2021; this application also claims priority from the U.S. provisional patent application Ser. No. 63/182,634 filed on Apr. 30, 2021; this application also claims priority from U.S. provisional patent application Ser. No. 63/182,637 filed on Apr. 30, 2021, all the three applications are incorporated herein by reference in its entirety.

FIELD OF INVENTION

The present invention relates to a system and method for visual field analysis for screening and monitoring vision disorders, and more particularly, the present invention relates to a moving pattern stimulation for visual field tests during retinal interrogation registered around the blind spot for visual field defect interrogation and exact spatial location.

BACKGROUND

The term visual field refers to how wide of an area an eye can see while focusing on a central point. Visual field assessments are performed to detect scotoma in the vision. Scotoma refers to a blind spot in the field of vision. Scotoma is a degenerated area in the field of vision surrounded by a field of normal vision.

Many diseases of the visual system first manifest as a selective geographic loss of vision at one or more locations. Many brain disorders can also result in blind spots in the vision. Visual field analysis is performed to screen a disease and monitor the progression of the disease during treatment. For example, Glaucoma is a progressive disease in which peripheral vision is lost due to damage in retinal ganglion cells, whose axons form the optic nerve. For example, primary open-angle glaucoma (POAG), which is estimated to affect several million in the United States, can lead to loss of vision if not detected early. Visual field analysis is typically used for detecting, monitoring disease progression, and evaluating new treatments for POAG and other visual disorders.

A visual field analysis also referred to as "perimetry," involves measuring how well a patient can see at various locations on his retina. Confrontation visual field test is a common way for testing vision field in a clinical setup, wherein a patient, having his one eye covered up or closed, focusses on an object. A doctor can hold up different numbers of fingers in areas of the peripheral visual field, wherein the patient while focusing on the object has to count the number of fingers. Another popular test is a static perimetry test, also performed in a clinical setup. The patient with one eye covered up must look at a center of a bowl-shaped instrument called a perimeter. In the test, small dim lights begin to appear in various places throughout the bowl. While keeping looking at the center target, the patient must report whenever he sees the dim light. Since the lights do not move, the test is referred to as the static perimetry test. Like the static perimetry test but having a moving light target is a Kinetic visual field test.

The visual field test is a subjective examination and depends much on the skills of the person administering the test as well as the understanding of the instructions by the patient. Moreover, the process of testing is tedious and requires the patient to visit a clinic. Going to clinic for visual field assessment can be a problem for home-bound patients. Moreover, the increasing adoption of telemedicine in the medical field mandates the need for newer methods of testing the visual field remotely.

Recently, there have been reports of methods for remotely testing the vison field through a computer screen. For example, Jones, P. R, Portable Perimetry Using Eye-Tracking on a Tablet Computer, A Feasibility Assessment, Trans. Vis. Sci. Tech. 2019; 8(1):17 reported an off-site flat-screen display test for visual field assessment. The known method of visual field assessment using a computer screen suffers from one major limitation i.e., requiring optimal luminance corrections and/or darkened room.

Thus, a need is appreciated for a system and method for visual field analysis that is devoid of the aforesaid drawbacks of traditional perimetry testing and modern computer-based remote testing.

Herein, the terms "testing", "assessing", "analysis", "assessment", and interrogation are interchangeably used to broadly refer to visual field analysis for screening any blind spots.

SUMMARY OF THE INVENTION

The following presents a simplified summary of one or more embodiments of the present invention to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a system and method for remotely assessing the visual field of a patient for screening any blind spots or monitoring the progression of any eye defect.

It is another object of the present invention that the system and method can be used to diagnose various eye conditions and brain disorders.

It is still another object of the present invention that the system and method can be used for self-diagnosis without requiring any external help.

It is yet another object of the present invention that the disclosed system and method can be cost-effective to use.

It is a further object of the present invention that the size of the blind spot can be determined.

It is still a further object of the present invention that the disclosed system and method may not require any specific setup and can be performed in ordinary room light.

In one aspect, disclosed is a system and method for assessing visual field of a subject eye of a user for any blind spots. The method includes the steps of presenting a screen that is rendered as a grid, wherein points of the grids are spaced in units of visual angle. A visual focus point is presented on the screen on the screen and a visual stimulus moves on the screen consecutively while the subject eye focuses on the visual focus point and tracks the movement of the visual stimulus. When the visual stimulus enters a blind spot area in the visual field, the movement of the visual stimulus is perceived to be halted but is moving. Upon exiting the blind spot area, the halted visual stimulus is perceived to start moving again. Inputs from the user are taken when the above two events occur. Based on the inputs, the area of the blind spot is mapped.

In one aspect, disclosed is a method for assessing visual field of a subject eye of a user, the method implemented within a system comprising a processor and a memory, the method comprising the steps of presenting a screen, by an interface module implemented within the system and upon processing by the processor, on a display, the screen is rendered as a grid of rows and columns, and cells at the intersection of the rows and the columns, the cells are of square shape, wherein a dimension of each cell is defined in units of visual angle; presenting, by the interface module, a visual focus point on the screen, wherein a location of the visual focus point depends on whether the subject eye is a left eye or a right eye; presenting a visual stimulus on the screen and within a cell of the grid; moving, by an analysis module implemented within the system and upon processing by the processor, the visual stimulus consecutively in a row at a predetermined speed, while the subject eye is focused on the visual focus point; receiving, by the analysis module, a first input from the user, wherein the first input is indicative of a first location of the visual stimulus in the row when the movement of the visual stimulus is perceived by the subject eye to suddenly halt, however the visual stimulus is continuously moving at the predetermined speed; receiving, by the analysis module, a second input from the user, wherein the second input is indicative of a second location of the visual stimulus in the row when the perceived halted visual stimulus is perceived by the subject eye as started moving; moving, by the analysis, the visual stimulus consecutively in a column at the predetermined speed, while the subject eye is focused on the visual focus point; receiving, by the analysis module, a third input from the user, wherein the third input is indicative of a third location of the visual stimulus in the column when the movement of the visual stimulus is perceived by the subject eye to suddenly halt, however the visual stimulus is continuously moving at the predetermined speed; receiving, by the analysis module, a fourth input from the user, wherein the fourth input is indicative of a fourth location of the visual stimulus in the column when the perceived halted visual stimulus is perceived by the subject eye as started moving; and determining, by the analysis module, an area of the blind spot in the subject eye by mapping the first location, the second location, the third location, and the fourth location in the grid relative to the location of the visual focus point, wherein each of the first location, the second location, the third location, and the fourth location are represented in the units of visual angle.

In one implementation of the method, the method further comprises the steps of obtaining, by a registration module implemented within the system and upon processing by the processor, a plurality of properties of a display, the plurality of properties comprises an effective size of the display; and determining, by the registration module, a desired distance range of the subject eye from the display based on the plurality of properties.

In one implementation of the method, the subject eye is the left eye, the visual focus point is positioned on a right side of the screen, the visual stimulus moves from right to left in the row.

In one implementation of the method, the subject eye is the right eye, the visual focus point is positioned on a left side of the screen, the visual stimulus moves from left to right in the row.

In one implementation of the method, the visual stimulus moves cell by cell and row by row from left to right or from right to left, wherein the visual stimulus moves cell by cell and column by column from top to bottom.

In one implementation of the method, the analysis module is configured to cause the visual stimulus to skip one or more cells in a repeated pattern or a predetermined pattern.

In one implementation of the method, the visual stimulus is rendered by highlighting boundaries of the cells, wherein the visual stimulus has a contrasting color relative to a color of a background of the screen.

In one implementation of the method, the visual stimulus moves in the row or the column consecutively leaving a visual trail, wherein the visual trail disappears when the visual stimulus moves to a next row or to a next column.

In one implementation of the method, the method further comprises the steps of determining, by the registration module, a distance of the subject eye from the display; and upon determining the distance, comparing the distance with the desired distance range; and upon comparing, generating a first feedback indicating whether the distance is within the desired distance range.

In one implementation of the method, the method further comprises the steps of determining, by the registration module, an undesired movement of the subject eye while the subject eye must be focused on the visual focus point; and upon determining the undesired movement, generating a second feedback indicative of the undesired movement of the subject eye.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting of embodiments of the invention. As used herein, the singular forms "a", "an", and "the" are intended to include the plural forms as well, unless the context indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

Disclosed is a system and method for analyzing a visual field of a person to screen a for blind spot or diagnose any medical condition related to vision and/brain, such as glaucoma. The disclosed system and method permit administering the test remotely, wherein persons in the comfort of their home can do self-diagnosing using the disclosed system and method. No special setup or changing the room lights may be required. For example, the test can be performed in ordinary room lights and may not require dark rooms. Moreover, any existing setup at the home or office of a person can be used, such as a desktop computer with an LCD, a tablet computer, or a laptop can be used. The patients can be saved from traveling to a clinic and waiting for hours for the diagnosis. The disclosed system and method can allow persons to self-diagnose eye defects or monitor existing scotoma/blind spots, at the comfort of their home and at any desired time.

Figure 1:
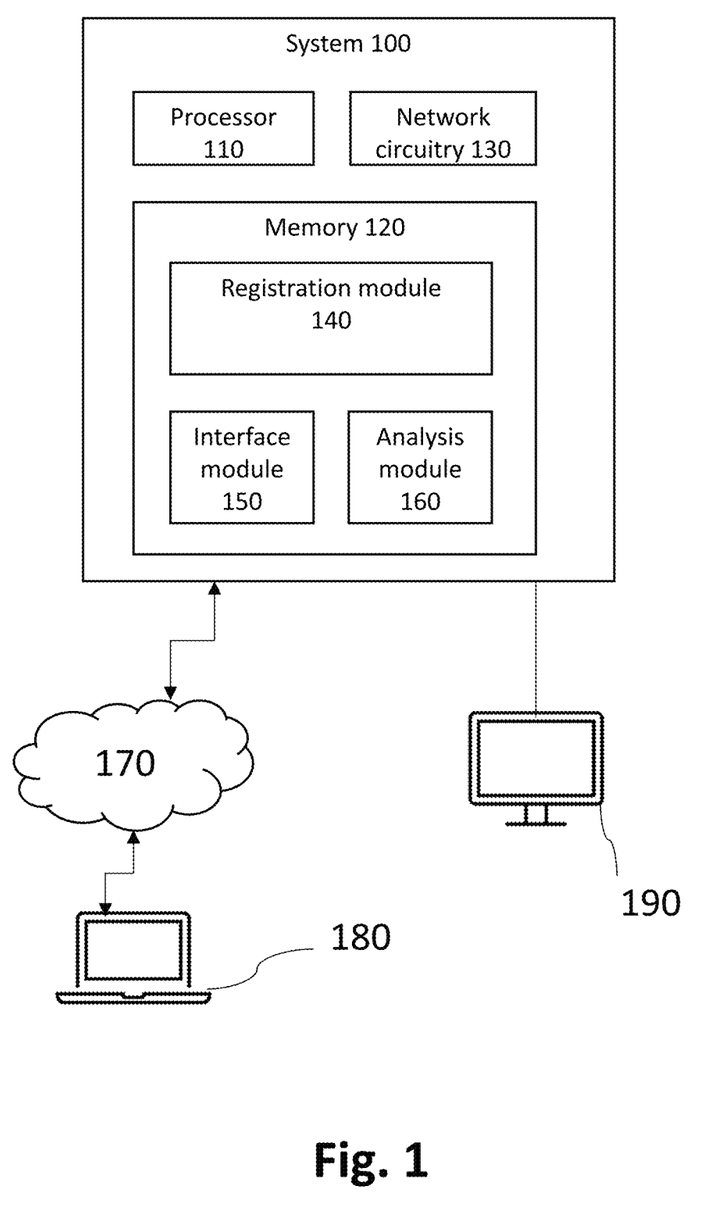
FIG. 1 is a block diagram illustrating the architecture and environment of the disclosed system, according to an exemplary embodiment.

Referring to FIG. 1, which is a block diagram illustrating an exemplary embodiment of the system 100 according to the present invention. The system 100 can include a processor 110 and a memory 120. The processor can be any logic circuitry that responds to, and processes instructions fetched from the memory. The memory may include one or more memory chips capable of storing data and allowing any storage location to be directly accessed by the processor. The system can also include a network circuitry 130 for connecting to a network 170. The network can be wired, wireless network, or a combination of wired and wireless networks. The wired network may include DSL and optical fiber lines. The wireless network may include Bluetooth®, Wi-Fi, WiMAX, and cellular networks including GPRS, LTE, CDMA, 3G, 4G, and 5G. The network can be a secure network, an unsecured network, or a combination of both. The system 100 can connect to one or more remote devices 180 through the network 170. While FIG. 1 shows a single network and a single device, however, it is understood that more than one device can simultaneously connect to the disclosed system through different networks, and a single device can connect with the system through more than one network. For example, a device can connect to the disclosed system through a combination of wired and wireless networks. The device can be a device that includes a display, such as a laptop computer, a desktop computer with a monitor, a tablet computer, and the like. Preferably, the size of the display can be large, such as more than 15 inches. The device can also include network circuitry for connecting to the disclosed system. the system can also be connected to a display 190.

As shown in FIG. 1, the memory includes modules according to the present invention for execution by the processor to perform one or more steps of the disclosed methodology. The memory can include a registration module 140, an interface module 150, an analysis module 160. The registration module upon execution by the processor can input details of the user and guide the user to have a posture suitable for the test. The interface module upon execution by the processor can present an interface for interacting with the user. The analysis module, upon execution by the processor, can detect blind spots or any other eye/brain disorder. The "user" herein refers to a person using or willing to use the disclosed system and method for visual field assessment. Optionally, application software can be provided on the device. The application software can be developed for the different operating systems, such as but not limited to Android™, iOS™, Windows™, Linux, macOS™, or any other known operating platform. In addition to the application software, a website-based interface can also be provided through the world-wide-web. While FIG. 1 shows the system and device as separate objects, however, the system and device can be one. When the system and device are separate, one or more modules of the system or one or more steps of the disclosed methodology can also be implemented on the device, without departing from the scope of the present invention. The system can also be implemented in a server environment including cloud servers. The server can include more than one server located in one place or geographically scattered at different places. Also, not shown in the drawings, the disclosed system can also connect with other devices, such as a device of a health care professional for sharing the diagnosis or a service provider responsible for storing the medical history of the user.

The registration module can take basic details of the patient, through an interface generated by the interface module. The basic details can be optional and can include name, age, gender, and the like. The registration module can also intake the medical history of the user related to the eyes and brain. Also, the details of any previous screening tests for the blind spots taken by the user can be received by the registration module, however, such details are optional. The registration module can detect properties of the display of the device being used by the user. The properties include at least an effective size of the display, resolution of the display, and pixel density. The registration module can also guide the user to position his head relative to the display. The head of the user should be at a predetermined distance from the display. This distance can be calculated by the registration module based on a predefined rule and the detected properties of the display. For example, the optimal distance between an eye and the screen can be about twelve to thirty-six inches. The optimum distance can be absolute or approximate, and deviations in the distance from the absolute optimum distance are within the scope of the present invention. In a preferred embodiment, when the position of the subject eye is at a distance of about twelve inches from the screen, the entire peripheral visual field can be accommodated inside the field of view on a seventeen inches computer display screen and this closer distance setting may be preferable especially when targeting the temporal crest region of the peripheral visual field. Therefore, the optimum distance of the subject eye from the screen may depend upon the effective size of the display.

In certain embodiment, the registration module can also guide the user in positioning his head relative to the screen. Moreover, the registration module can also optionally detect undesired head movements or eye movements during the test. For example, the registration module can use the camera of the device to detect the distance of the head or eyes from the display. Moreover, the camera of the device can be used to detect undesired head movements or eye movements. In one case, the user may be instructed by the registration module to move his head in a predetermined manner to detect the distance of the head from the display. Alternatively, a chin rest with a scale can be provided, and the user can extend the chin head from the display up to the desired distance and can then rest his chin upon the chin rest, thus immobilizing the head. Alternatively, suitable sensors can also be used to detect the distance between the head and the display. For example, a sensor can be coupled to the forehead of the user. The sensors can optionally work with the camera of the display to determine the distance. Any other mechanism to determine the distance of the head from the display is within the scope of the present invention. The chin rest can also include sensors to detect the distance of the chin rest from the display. LIDAR and similar techniques can also be used to determine the distance between the head of the user and the display. Also are known eye-tracking glasses and head mounts that can be used to determine eye movements and optionally measure the distance from the display. Also, a stimulus flash at a known distance from the fixation spot can be provided wherein the user at the desired distance cannot see the flash—but can see the flash when at the wrong distance. The registration module can monitor the undesired head and eye movements during the test and can provide suitable feedback, such as audio feedback in case the undesired movements are detected.

Figure 2:
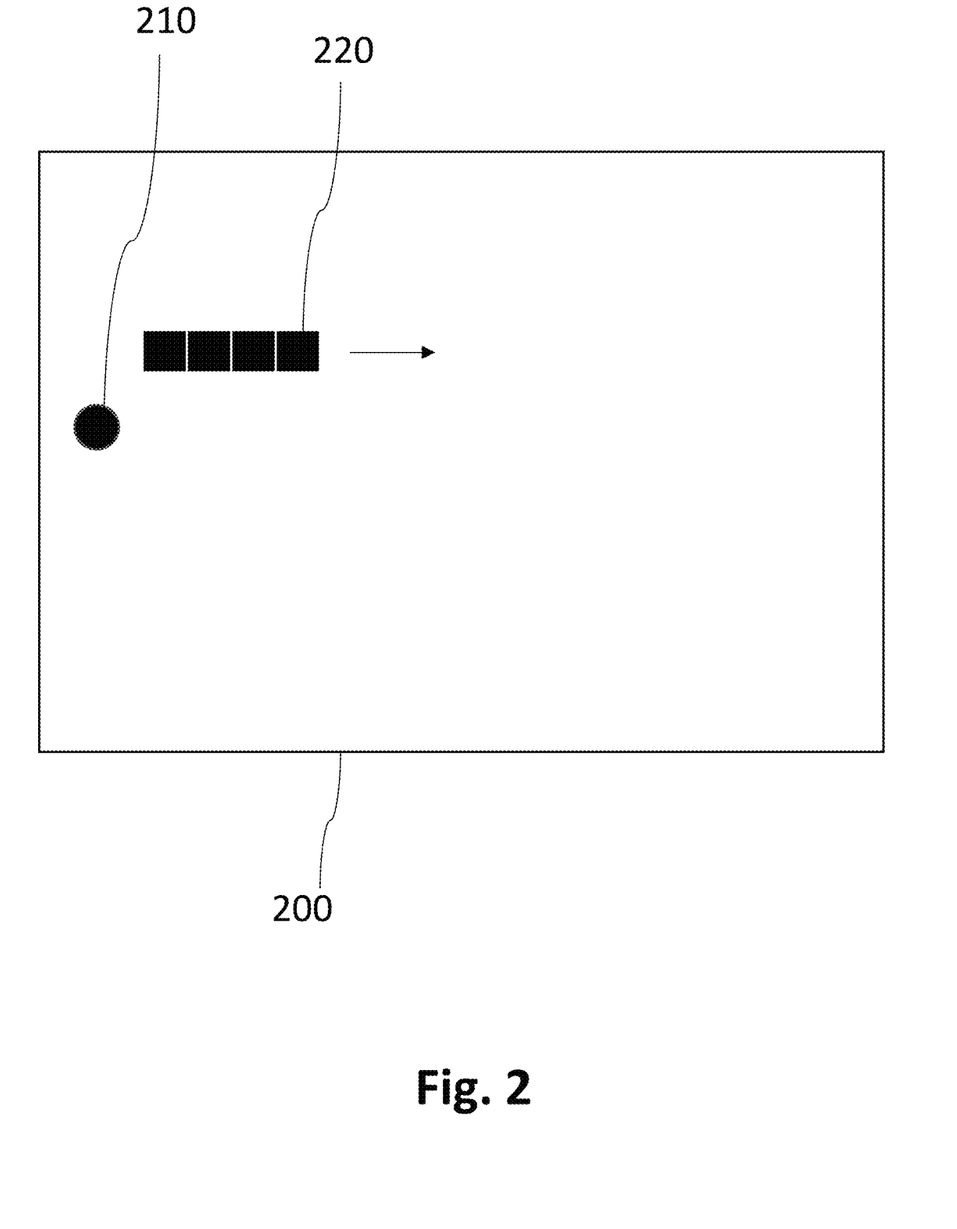
FIG. 2 shows a screen of the interface, according to an exemplary embodiment.

The interface module can provide an interface to receive details from the user as well as to provide instructions and results to the user. Through the interface, the user can interact with the system. The interface can provide a screen implemented on the display for performing the visual field assessment. An embodiment of the screen is shown in FIG. 2. The screen 200 can be virtually divided into a grid having rows and columns, and cells as an intersection of the row and column. However, such a grid may not be visible to the eyes but the screen can have a plain background. Preferably, the background can be white, however, any color of the background is within the scope of the present invention. Moreover, any pattern as the background is also within the scope of the present invention. A visual stimulus 220 can also be implemented by the interface module on the screen, wherein the visual stimulus can move from left to right or right to left, and from top to bottom of the screen. In certain implementations, the visual stimulus can be a box of a size depending upon the resolution and pixel density of the display. The box can be of a contrasting color relative to the background of the screen. Preferably, the box can be square and black, however, any other shape and contrasting color of the visual stimulus is within the scope of the present invention.

In certain implementations, the visual stimulus can move along rows from left to right or right to left, along with columns from the top to bottom. For a given test, the visual stimulus may however move only from left to right or right to left but not both. The visual stimulus can move cell by cell and row by row from left to right or right to left. Also, the visual stimulus can move cell by cell and column by column from top to bottom. However, one or more cells, or one or more rows, or one or more columns can be skipped by the visual stimulus in a repeated manner or a predetermined pattern without departing from the scope of the present invention. Thus, the visual stimulus can move two cells at a time without departing from the scope of the present invention. Also, it is to be noted that the movement of the visual stimulus vertically from the bottom to the top is also within the scope of the present invention.

In certain implementations, the visual stimulus can move consecutively in a row or column to form a visual line. The visual line starts at an edge or end of a row or column and extends up to the opposite edge or end of the respective row or column. FIG. 2 shows the box shape visual stimulus moving in a contiguous manner forming a visible trail that starts from the left towards the right, i.e., a visible row/line can be presented by the interface module. However, a previous visual line may disappear when a new visual line begins.

The interface module can also present a visual focus point 210 on screen 200. The visual focus point can also be of a contrasting color relative to the background of the screen. In one case, the visual focus point and the visual stimulus can be of the same color. Alternatively, the visual focus point and the visual stimulus can be of a different color. The visual focus point shown in FIG. 2 is of a solid bullet shape, however, any other size and shape of the visual focus point are within the scope of the present invention. Any animated icon as the visual focus point is also within the scope of the present invention. The position of the visual focus point can depend upon the eye to be tested. The eye of the user to be tested using the disclosed system is also referred to herein as the subject eye. In one case, when the subject eye is a left eye, the visual focus point can be on the right side of the screen. Similar, when the subject eye is the right eye, the visual focus point can be on the left side of the screen. FIG. 2 shows the visual focus point on the left of the screen for the right side subject eye.

Figure 3:
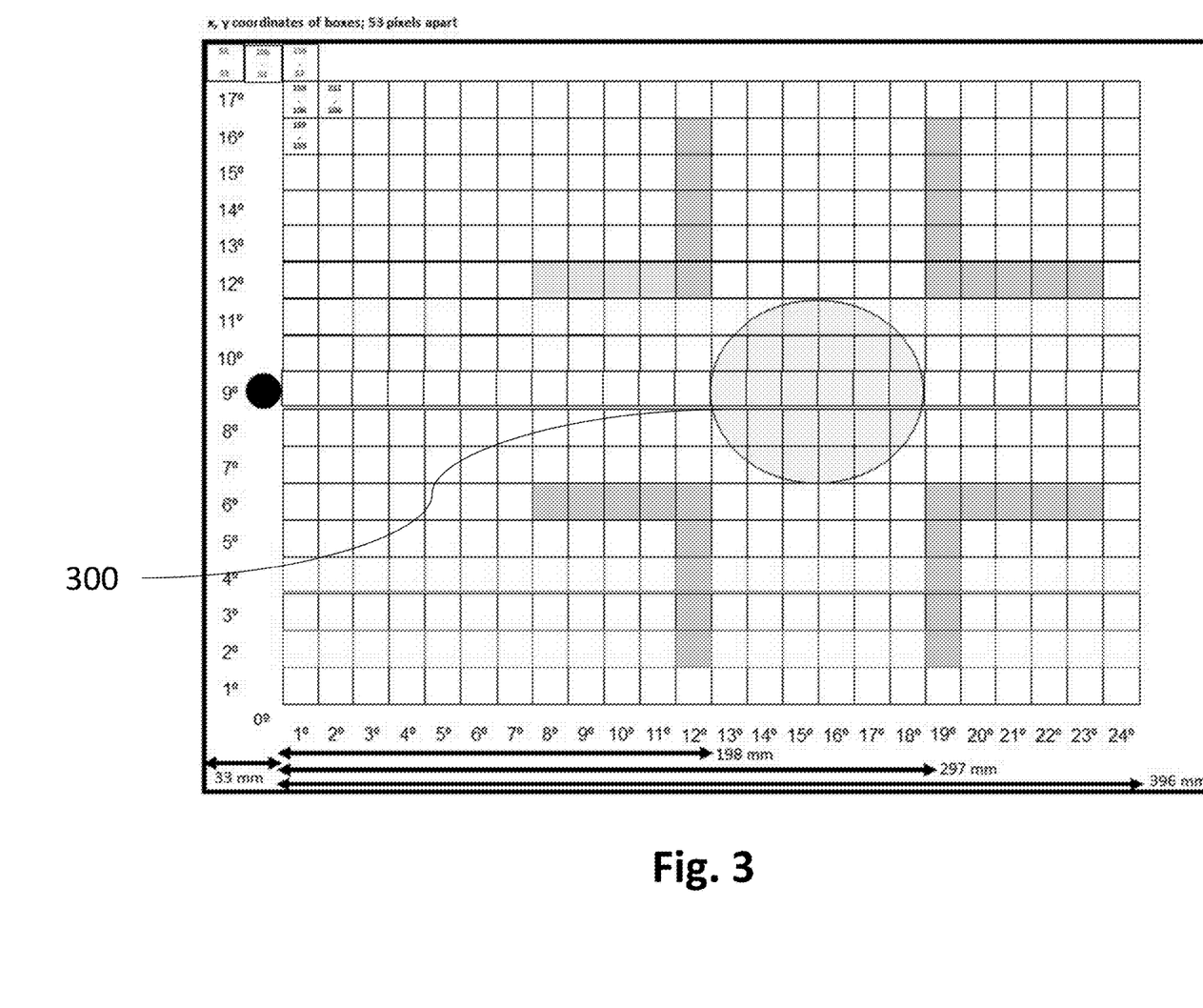
FIG. 3 illustrates the mapping of a blind spot using the disclosed system and method, according to an exemplary embodiment of the present invention.

To perform the test, the eye of the user other than the subject eye can be covered up. The user can position his head at the desired distance. Thereafter, the user can focus, through the subject eye, on the visual focus point. While keeping the focus on the visual focus point, the analysis module, through the interface module, can cause the visual stimulus to move on the screen in any of the patterns as described above. The visual stimulus can first move horizontally and then vertically, or the visual stimulus can first move vertically and then horizontally. The visual stimulus is visible to the subject eye while being focused on the visual focus point. The subject eye can also perceive the movement of the visual stimulus on the screen. The subject eye while being focused on the visual focus point can track the movement of the visual stimulus. However, when the visual stimulus enters into a blind spot area of the field of the vision of the subject eye, the subject eye perceives that the visual stimulus has stopped moving which is otherwise moving. The visual stimulus can still be visible to the user but perceived as stationary. When the visual stimulus exits the blind spot, the visual stimulus can be perceived by the eye as having started to move again. The analysis module can receive input from the user when the moving visual stimulus is perceived by the subject eye to be stopped suddenly. A second input is received from the user by the analysis module when the stopped visual stimulus is perceived by the subject eye to have started moving again suddenly. The input from the user can be taken using any input device coupled to the device of the user, such as a mouse. The user can click to provide the input. Using the two consecutive inputs from horizontal and vertical moving visual stimulus, an area of the blind spot 300 can be mapped by the analysis module, as shown in FIG. 3. In FIG. 3, a full HD monitor of 27 inches (diagonal) is used for the study. The pixel dimensions can be 0.311 mm×0.311 mm, 3.23 pixels per mm (82 pixels per inch). The following Resolution may be used for the Blind-Spot Location Test: 1° of visual angle=1 box=53 pixels=16.5 mm (Stroke (border) of each box to overlap with the stroke of adjacent boxes). The Most-Probable Locus of Blind Spot: can be between 12° to 18° along the X-axis and 2° to 3° visual degrees on either side of the equator. For the test, the Right Eye (to be tested) must be perpendicular to the Display surface, and in line with the visual stimulus (53-pixel dia.) on the left edge of the display.

Figure 4:
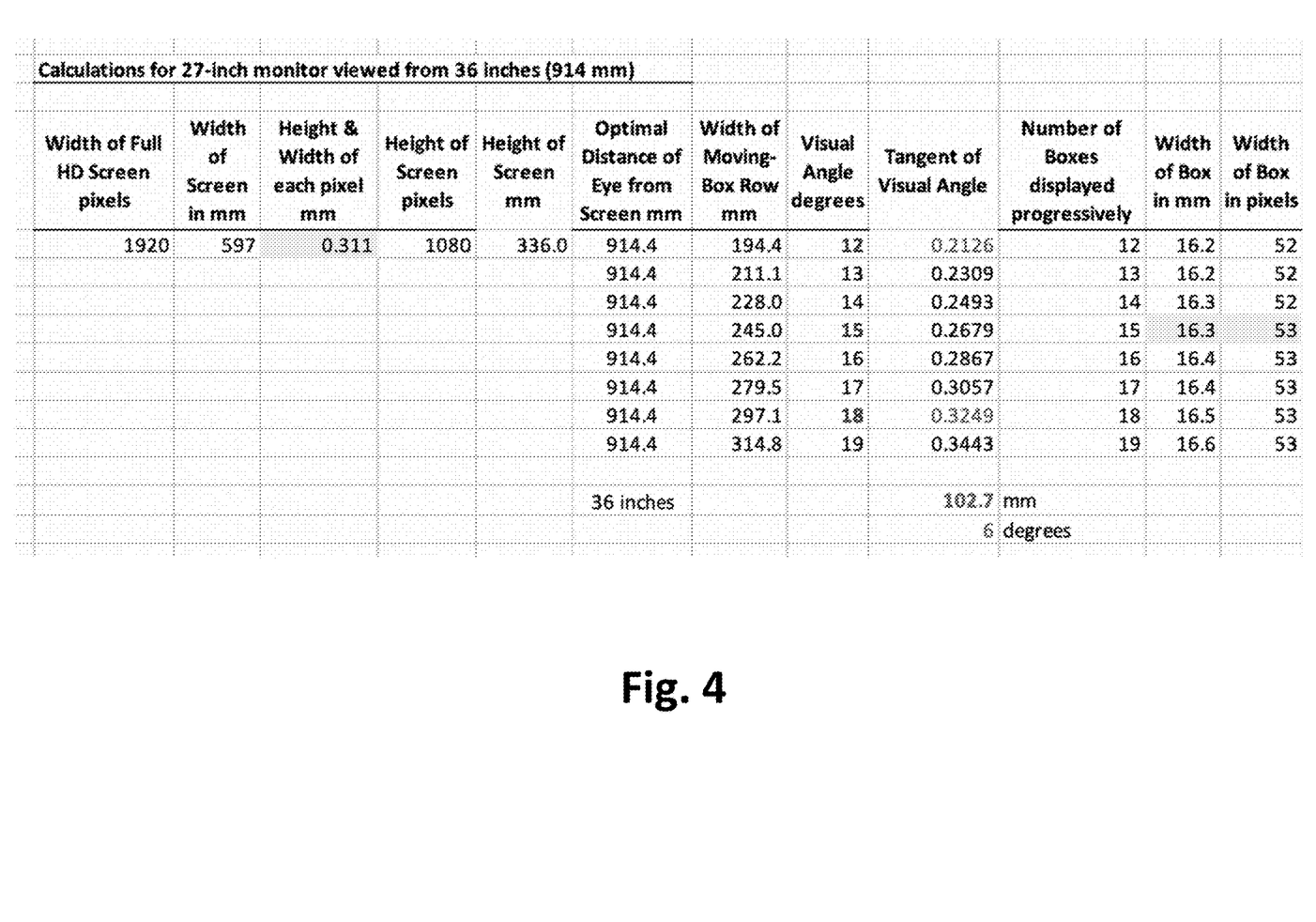
FIG. 4 shows different parameters in the mapping of a blind spot, according to an exemplary embodiment of the present invention.

FIG. 4 shows different parameters taken into consideration for mapping the blind spot. The area of the blind spot in the form of a map can be displayed by the analysis module through the interface module. The results can also be shared in different forms, such as PDF, JPG, or any dynamic format, and the results can also be transmitted to other devices, through FTP, HTTP, Email, and the like internet protocols.

The analysis module can also determine the response time of the user, i.e., the difference between the time at which the sudden stop or restarting of the movement of the visual stimulus is perceived by the eye and the time at which the input is received by the analysis module. For example, the analysis module can stop the moving visual stimulus and move the stopped visual stimulus randomly while the subject eye is focused on the visual focus point. The time taken by the user to provide the input can be averaged out to obtain the response time.

Again, referring to FIG. 4, it can be seen that the size of the visual stimulus, such as a blinking square can be proportional to the distance of the user's head from the screen. Optionally, the user can have the freedom to choose the distance or choose the distance from a predefined range. FIG. 4 shows the calculations done for a distance of thirty-six inches i.e., 914 mm. The visual angle can be calculated as the tangent inverse of the length and/or breadth of the screen divided by the distance from the screen.

In certain implementations, the disclosed system and method can be used to diagnose disorders where there is pathology in the retina, such as glaucoma, Brain Tumors, or Retinitis Pigmentosa, and like eye and brain disorders. The disclosed system and method have the advantage that the performance of the tests may not need adjustment for ambient luminosity nor require a darkened room. The test can be displayed on a flat screen (rather than a curved perimetric bowl) with emphasis on the peripheral location of the visual field test points being displayed consistent with the temporal crest projection, outside the "central" region at the fovea onto the nasal retinal regions. This region, representing the peripheral Visual Field after the projected Vision Cone inverts all 3 axes in image representation derives from the proposed topological model of Visual Field representation. Importantly, the disclosed system and method can be easy to translate to an internet-connected computer screen display module for home testing.

In certain implementations, the visual stimulus can be animated, such as blink. For example, a blinking square can be presented on the screen, wherein the blinking square forms a horizontal line that gradually extends from one side of the screen to the other at 2° per second. The moving and blinking square is normally visible to the subject eye as it extends towards the blind spot. However, as it passes the Blind Spot region, instead of disappearing from the view, the square may seem to halt and will pick up movement once the square passes out of the blind spot. It is anticipated a similar result if the moving stimulus passes a region (including glaucomatous damage)—and importantly, the test point will always be visible. An undetected signal by the user cannot be misinterpreted as a mistake on their part.

What is claimed is:
1. A method for assessing visual field of a subject eye of a user, the method implemented within a system comprising a processor and a memory, the method comprising the steps of:
   presenting a screen, by an interface module implemented within the system and upon processing by the processor, on a display, the screen is rendered as a grid of rows and columns, and cells at intersection of the rows and the columns, the cells are of square shape, wherein a dimension of each cell is defined in units of visual angle;
   presenting, by the interface module, a visual focus point on the screen, wherein a location of the visual focus point depends on whether the subject eye is a left eye or a right eye;
   presenting a visual stimulus on the screen and within a cell of the grid;
   moving, by an analysis module implemented within the system and upon processing by the processor, the visual stimulus consecutively in a row at a predetermined speed, while the subject eye is focused on the visual focus point;
   receiving, by the analysis module, a first input from the user, wherein the first input is indicative of a first location of the visual stimulus in the row when the movement of the visual stimulus is perceived by the subject eye to suddenly halt, however the visual stimulus is continuously moving at the predetermined speed;
   receiving, by the analysis module, a second input from the user, wherein the second input is indicative of a second location of the visual stimulus in the row when the perceived halted visual stimulus is perceived by the subject eye as started moving;
   moving, by the analysis module, the visual stimulus consecutively in a column at the predetermined speed, while the subject eye is focused on the visual focus point;
   receiving, by the analysis module, a third input from the user, wherein the third input is indicative of a third location of the visual stimulus in the column when the movement of the visual stimulus is perceived by the subject eye to suddenly halt, however the visual stimulus is continuously moving at the predetermined speed;
   receiving, by the analysis module, a fourth input from the user, wherein the fourth input is indicative of a fourth location of the visual stimulus in the column when the perceived halted visual stimulus is perceived by the subject eye as started moving; and
   determining, by the analysis module, an area of a blind spot in the subject eye by mapping the first location, the second location, the third location, and the fourth location in the grid relative to the location of the visual focus point, wherein each of the first location, the second location, the third location, and the fourth location are represented in the units of visual angle.

2. The method according to claim 1, wherein the method further comprises the steps of:
   obtaining, by a registration module implemented within the system and upon processing by the processor, a plurality of properties of a display, the plurality of properties comprises an effective size of the display; and determining, by the registration module, a desired distance range of the subject eye from the display based on the plurality of properties.

3. The method according to claim 2, wherein the method further comprises the steps of:

determining, by the registration module, a distance of the subject eye from the display; and upon determining the distance, comparing the distance with the desired distance range; and upon comparing, generating a first feedback indicating whether the distance is within the desired distance range.

4. The method according to claim 3, wherein the method further comprises the steps of:

determining, by the registration module, an undesired movement of the subject eye while the subject eye must be focused on the visual focus point; and upon determining the undesired movement, generating a second feedback indicative of the undesired movement of the subject eye.

5. The method according to claim 1, wherein the subject eye is the left eye, the visual focus point is positioned on a right side of the screen, the visual stimulus moves from right to left in the row.

6. The method according to claim 1, wherein the subject eye is the right eye, the visual focus point is positioned on a left side of the screen, the visual stimulus moves from left to right in the row.

7. The method according to claim 1, wherein the visual stimulus moves cell-by-cell and row-by-row from left to right or from right to left, wherein the visual stimulus moves cell by cell and column by column from top to bottom.

8. The method according to claim 7, wherein the analysis module is configured to cause the visual stimulus to skip one or more cells in a repeated pattern or a predetermined pattern.

9. The method according to claim 1, wherein the visual stimulus is rendered by highlighting boundaries of the cells, wherein the visual stimulus has a contrasting color relative to a color of a background of the screen.

10. The method according to claim 1, wherein the visual stimulus moves in the row or the column consecutively leaving a visual trail, wherein the visual trail disappears when the visual stimulus moves to a next row or to a next column.

11. A system for assessing visual field of a subject eye of a user, the system comprising a processor and a memory, the system configured to implement a method comprising the steps of:

presenting a screen, by an interface module implemented within the system and upon processing by the processor, on a display, the screen is rendered as a grid of rows and columns, and cells at intersection of the rows and the columns, the cells are of square shape, wherein a dimension of each cell is defined in units of visual angle;

presenting, by the interface module, a visual focus point on the screen, wherein a location of the visual focus point depends on whether the subject eye is a left eye or a right eye;

presenting a visual stimulus on the screen and within a cell of the grid;

moving, by an analysis module implemented within the system and upon processing by the processor, the visual stimulus consecutively in a row at a predetermined speed, while the subject eye is focused on the visual focus point;

receiving, by the analysis module, a first input from the user, wherein the first input is indicative of a first location of the visual stimulus in the row when the movement of the visual stimulus is perceived by the subject eye to suddenly halt, however the visual stimulus is continuously moving at the predetermined speed;

receiving, by the analysis module, a second input from the user, wherein the second input is indicative of a second location of the visual stimulus in the row when the perceived halted visual stimulus is perceived by the subject eye as started moving;

moving, by the analysis module, the visual stimulus consecutively in a column at the predetermined speed, while the subject eye is focused on the visual focus point;

receiving, by the analysis module, a third input from the user, wherein the third input is indicative of a third location of the visual stimulus in the column when the movement of the visual stimulus is perceived by the subject eye to suddenly halt, however the visual stimulus is continuously moving at the predetermined speed;

receiving, by the analysis module, a fourth input from the user, wherein the fourth input is indicative of a fourth location of the visual stimulus in the column when the perceived halted visual stimulus is perceived by the subject eye as started moving; and determining, by the analysis module, an area of a blind spot in the subject eye by mapping the first location, the second location, the third location, and the fourth location in the grid relative to the location of the visual focus point, wherein each of the first location, the second location, the third location, and the fourth location are represented in the units of visual angle.

12. The system according to claim 11, wherein the method further comprises the steps of:

obtaining, by a registration module implemented within the system and upon processing by the processor, a plurality of properties of a display, the plurality of properties comprises an effective size of the display; and determining, by the registration module, a desired distance range of the subject eye from the display based on the plurality of properties.

13. The system according to claim 12, wherein the method further comprises the steps of:

determining, by the registration module, a distance of the subject eye from the display; and upon determining the distance, comparing the distance with the desired distance range; and upon comparing, generating a first feedback indicating whether the distance is within the desired distance range.

14. The system according to claim 13, wherein the method further comprises the steps of:

determining, by the registration module, an undesired movement of the subject eye while the subject eye must be focused on the visual focus point; and upon determining the undesired movement, generating a second feedback indicative of the undesired movement of the subject eye.

15. The system according to claim 11, wherein the subject eye is the left eye, the visual focus point is positioned on a right side of the screen, the visual stimulus moves from right to left in the row.

16. The system according to claim 11, wherein the subject eye is the right eye, the visual focus point is positioned on a left side of the screen, the visual stimulus moves from left to right in the row.

17. The system according to claim 11, wherein the visual stimulus moves cell by cell and row by row from left to right or from right to left, wherein the visual stimulus moves cell by cell and column by column from top to bottom.

18. The system according to claim 17, wherein the analysis module is configured to cause the visual stimulus to skip one or more cells in a repeated pattern or a predetermined pattern.

19. The system according to claim 11, wherein the visual stimulus is rendered by highlighting boundaries of the cells, wherein the visual stimulus has a contrasting color relative to a color of a background of the screen.

20. The system according to claim 11, wherein the visual stimulus moves in the row or the column consecutively leaving a visual trail, wherein the visual trail disappears when the visual stimulus moves to a next row or to a next column.

\* \* \* \* \*